(12) United States Patent
Takakusaki et al.

(10) Patent No.: US 6,643,009 B2
(45) Date of Patent: Nov. 4, 2003

(54) METHOD OF INSPECTING A WRAP-FITTED STATE OF A CAP WRAP-FITTED TO A NECK OF A BOTTLE AND APPARATUS THEREFOR

(75) Inventors: Nobuyuki Takakusaki, Hiratsuka (JP); Yukihito Nozaki, Hiratsuka (JP); Yukio Yoshikawa, Zana (JP); Kazunori Nousou, Yokohama (JP)

(73) Assignee: Japan Crown Cork Co. Ltd., Tokyo (JP)

( * ) Notice: Subject to any disclaimer, the term of this patent is extended or adjusted under 35 U.S.C. 154(b) by 0 days.

(21) Appl. No.: 10/175,289

(22) Filed: Jun. 20, 2002

(65) Prior Publication Data

US 2002/0196434 A1 Dec. 26, 2002

(30) Foreign Application Priority Data

Jun. 20, 2001 (JP) ........................................ 2001-187168
Feb. 19, 2002 (JP) ........................................ 2002-040981
Mar. 25, 2002 (JP) ........................................ 2002-084314

(51) Int. Cl.[7] ............................................. G01N 21/00
(52) U.S. Cl. ................................ 356/240.1; 356/239.4; 356/239.5; 356/239.6
(58) Field of Search ............................. 356/240.1, 239.1, 356/239.2, 239.4, 239.5, 239.6, 239.7, 239.8; 250/559.05, 559.07, 559.46, 223 B, 223 R (56) References Cited

U.S. PATENT DOCUMENTS

| | | | | | |
|---|---|---|---|---|---|
| 4,606,635 | A | * | 8/1986 | Miyazawa et al. | 356/240.1 |
| 4,746,212 | A | * | 5/1988 | Sudo et al. | 356/240.1 |
| 4,868,404 | A | * | 9/1989 | Hajime | 250/223 B |
| 5,592,286 | A | * | 1/1997 | Fedor | 356/240.1 |
| 6,072,575 | A | * | 6/2000 | Loll | 356/239.2 |
| 6,122,048 | A | * | 9/2000 | Cochran et al. | 356/240.1 |
| 6,275,287 | B1 | * | 8/2001 | Watanabe | 356/239.4 |

FOREIGN PATENT DOCUMENTS

DE   299 07 762   * 10/1999

* cited by examiner

Primary Examiner—Frank G. Font
Assistant Examiner—Sang H. Nguyen
(74) Attorney, Agent, or Firm—Sherman & Shalloway (57) ABSTRACT

A method of inspecting a wrap-fitted state of a cap that is wrap-fitted to the neck of a bottle by detecting a positional relationship between a bottle mark and a cap mark, wherein an optical lens is arranged at a higher position on the vertical center axis of the bottle to which the cap is wrap-fitted, a single camera is arranged at a higher position on the optical axis of the optical lens to image the bottle mark and the cap mark through the optical lens, an illumination device is arranged for illuminating the bottle mark and the cap mark, the bottle mark and the cap mark are simultaneously shot by the camera, and the obtained image is sent to an image processor to detect a positional relationship between the bottle mark and the cap mark.

16 Claims, 9 Drawing Sheets

CAMERA IMAGE

EXPANSION OF
THE POLAR COORDINATE

FIG.13

CAMERA IMAGE

EXPANSION OF
THE POLAR COORDINATE

METHOD OF INSPECTING A WRAP-FITTED STATE OF A CAP WRAP-FITTED TO A NECK OF A BOTTLE AND APPARATUS THEREFOR

BACKGROUND OF THE INVENTION

1. Field of the Invention

The present invention relates to a method of inspecting a wrap-fitted state (tightened state) of a cap wrap-fitted to the neck of a bottle and to an apparatus therefor. More specifically, the invention relates to a method capable of easily confirming a wrap-fitted state of a cap from one direction without opening the cap and to an apparatus therefor.

2. Description of the Related Art

In a bottle-cap assembly comprising a glass bottle or a plastic bottle and a cap having a tamper-evidence function for clearly indicating that the cap was once opened, it is essential that the cap is fitted in a completely sealed state after the content has been filled. So far, the fitted state was inspected by picking up some samples out of the products, really opening the cap to measure the torque for opening the cap and the angle of fitting.

However, the pick-up inspection is of a nature that is conducted for only some of the products. If the samples are picked up in a large number to improve the reliability of inspection, the cost of production increases correspondingly.

In the wrap-fitting machine used for wrap-fitting the cap to the neck of the bottle, further, the torque is determined at the time of setting, first, the wrap-fitting condition according to the wrap-fitting angle to ensure a basic sealing performance. It is therefore desired that the wrap-fitting angle be easily measured.

To solve this problem, there has been proposed a bottle-cap assembly which enables the fitted state of the cap to be easily confirmed.

For example, Japanese Unexamined Patent Publication No. 12046/1997 discloses a sealing device in which one or a plurality of position indicator marks are formed at predetermined positions lower than the lower end of a plastic cap in a state where the cap is completely screwed onto the neck of a container, and seal indicator marks are formed on a skirt of the cap so as to be located by the side of the position indicator marks in a state where the cap is completely screwed onto the neck of the container.

Japanese Unexamined Patent Publication No. 203512/1998 discloses a method of inspecting the sealed state of the neck of a container by arranging marks on the outer periphery of the container and on the outer surface of a screw cap screwed onto the neck of the container, the marks having a predetermined positional relationship with respect to the ends of the respective threaded portions, and judging whether the screwed state of the screw cap is proper based on the positional relationship of the pair of marks (mark of the container and mark of the screw cap) after the screw cap has been mounted.

Japanese Unexamined Patent Publication No. 11504/1999 discloses a structure for sealing bottles by providing marks that can be viewed from the outer side on a portion corresponding to the starting end of the threaded portion at the neck of the bottle and on a portion corresponding to the terminating end of the threaded portion of the cap, to inspect the degree of the cap wrap-fitted to the neck of the bottle relying upon the positions of these two marks after the bottle is filled with the liquid and is sealed.

Further, Japanese Unexamined Patent Publication No. 118515/2000 discloses an inspection method in which a portion of a cap mounted on the container body is imaged by using a camera, the imaged data is stored, and it is judged whether the mounting state of the cap is acceptable using the imaged data based upon a positional relationship between a reference position of the container body and a reference position of the cap. There has been described that the imaging is effected by using a first camera and a second camera arranged in parallel along the container conveyer passage.

According to the above prior arts, the fitted state of the bottle-cap assembly can be confirmed without relying upon the inspection method of picking up the samples and really opening the caps.

According to the sealing device of Japanese Unexamined Patent Publication No. 12046/1997, however, the marks formed on the bottle and on the cap must be positioned on a straight line or to establish a predetermined relationship, involving difficulty in setting the marks.

According to the method of inspecting the sealed state of Japanese Unexamined Patent Publication No. 203512/1998 and the sealing structure of Japanese Unexamined Patent Publication No. 11504/1999, a predetermined reference range is provided concerning the positional relationship of the cap and the bottle, and the bottle-cap assemblies outside this range are excluded. Therefore, there does not arouse the problem of the sealing device of Japanese Unexamined Patent Publication No. 12046/1997. In the bottle-cap assemblies disclosed in these prior arts, however, the mark of the cap is formed on the side surface of the cap due to the relationship to the bottle. In order to confirm that the marks of the bottle and of the cap are in a predetermined positional relationship, it is necessary to measure the mark from the side surface of the bottle-cap assembly. However, the bottle-cap assemblies filled with the content and sealed with the caps are conveyed on the conveyer along the production line while changing their directions in a random fashion, and the marks formed on the bottle and on the cap are not necessarily headed toward the inspection device. Therefore, failure in the fitted state of the cap is often overlooked decreasing the reliability of inspection.

In order to prevent the bottle-cap assemblies which are in a defectively fitted state from being overlooked, it is necessary to install a plurality of cameras in the circumferential direction, often causing the inspection device to become complex and making it difficult to continuously supply the bottle-cap assemblies.

When the mark (bottle mark) formed on the bottle and the mark (cap mark) formed on the cap are imaged by using a camera and the wrap-fitted state of the cap is inspected based on the obtained image, it is necessary that the two marks are vividly imaged. As for the bottle mark, however, it is often difficult to vividly image the bottle mark. That is, the bottle mark, in many cases, is formed on a portion on the outer surface of the neck of the bottle that is not covered with the cap, i.e., formed on a support ring. In many of the bottles, however, the neck portion equipped with a portion forming a bottle mark such as a support ring is whitened due to crystallization, or the whole bottle inclusive of the neck is formed transparent. When the bottle has the transparent neck, in particular, the bottle mark is not, in many cases, vividly imaged. The bottle wrap-fitted with the cap has been filled with the content liquid such as a beverage. However, since the neck of the bottle is transparent, the swinging level of the liquid in the bottle is reflected on the image caught by the camera and, as a result, the bottle mark is blurred.

SUMMARY OF THE INVENTION

It is therefore an object of the present invention to provide a method of inspecting a wrap-fitted state of a cap, which is capable of reliably confirming the wrap-fitted state of the cap that is fitted to the bottle from the upper side in the axial direction of the bottle without opening the cap, easily by using one camera, free of inconvenience involved in the prior art, and a device therefor.

Another object of the present invention is to provide a method of inspecting a wrap-fitted state of a cap by imaging the bottle mark and the cap mark by using a camera, wherein the bottle mark and the cap mark are vividly imaged even for transparent bottles having transparent necks irrespective of the kinds of the bottles, enabling the wrap-fitted state of the cap to be reliably inspected based upon the image processing.

According to the present invention, there is provided a method of inspecting a wrap-fitted state of a cap of a bottle-cap assembly in which the cap having a top panel and a skirt is wrap-fitted to a neck of a bottle, by detecting a positional relationship between a bottle mark formed on the bottle and a cap mark formed on the cap; wherein an optical lens is arranged at a higher position on the vertical center axis of said bottle-cap assembly in a manner that the vertical center axis is in agreement with an optical axis thereof;

a single camera is arranged at a higher position on the optical axis of said optical lens to image the bottle mark and the cap mark through the optical lens;

an illumination device is arranged for illuminating the bottle mark and the cap mark or the vicinities thereof; and the bottle mark and the cap mark are simultaneously shot by the camera, and the obtained image is sent to an image processor to detect a positional relationship between the bottle mark and the cap mark.

According to the inspection method of the present invention, the bottle mark and the cap mark are read out from the image data received by the image processor into polar coordinates with the cap as a center and, as required, are expanded to detect the positions thereof, the angle or the distance of expansion between the bottle mark and the cap mark is calculated, and whether the wrap-fitted state is acceptable is judged relying upon the angle or the expanded distance.

According to the inspection method of the present invention, further, it is desired that the illumination device is arranged to surround the optical lens, the optical path of light irradiated from said illumination device is so adjusted that the bottle mark and the cap mark are not directly irradiated with light but the portions of the skirt of the cap without forming the cap mark are directly irradiated with light, and the bottle mark and the cap mark are simultaneously shot by the camera while effecting the illumination by the illumination device under these conditions. Upon imaging the cap mark and the bottle mark under the above-mentioned illumination conditions, the cap mark and the bottle mark are vividly imaged even when the neck portion of the bottle inclusive of the support ring is transparent.

According to the present invention, further, there is provided a device for inspecting a wrap-fitted state of a cap of a bottle-cap assembly in which the cap is wrap-fitted to the neck of a bottle, by detecting a positional relationship between a bottle mark formed on the neck of the bottle and a cap mark formed on the cap, comprising:

an optical lens arranged at a higher position on the vertical center axis of said bottle-cap assembly in a manner that the optical axes thereof are in agreement;

a single camera for simultaneously shooting the bottle mark and the cap mark through said optical lens;

an illumination device for illuminating said bottle mark and said cap mark or the vicinities thereof; and an image processor for reading out the bottle mark and the cap mark from the image data shot by the camera, expanding, as required, the bottle mark and the cap mark to detect the positions thereof, calculating the angle or the distance of expansion between the bottle mark and the cap mark, and judging whether the wrap-fitted state is acceptable relying upon the angle or the expanded distance.

DETAILED DESCRIPTION OF THE INVENTION

Figure 1:
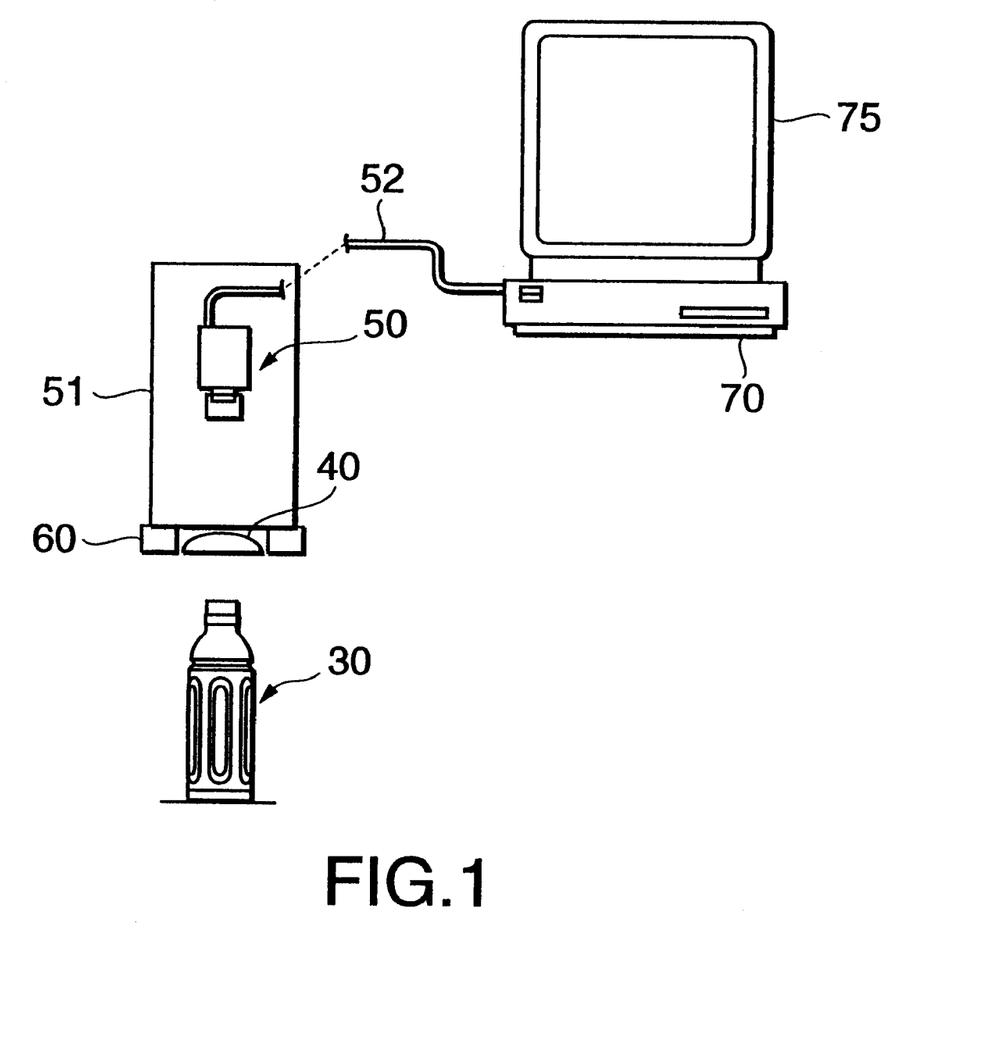
FIG. 1 is a view illustrating the arrangement of an inspection apparatus used for conducting the inspection method of the present invention.

FIG. 1 is a view illustrating the arrangement of the inspection device for conducting the inspection method of the present invention. At higher positions on the vertical axis of a bottle-cap assembly 30, there are arranged an optical lens 40 and a camera 50 having a CCD imaging element for imaging a cap mark formed on the cap and a bottle mark formed on the support ring of the bottle (these marks are not shown in FIG. 1), in a manner that the vertical axis of the assembly 30 is in agreement with the optical axis of the optical system (optical lens 40 and camera 50).

An illumination device 60 is circularly arranged to surround the optical lens 40.

The camera 50 is accommodated in a cylindrical hood 51 of which the lower end is opened. The lens 40 is arranged at the center of the opening of the hood 51, and an optical path between the lens 40 and the camera 50 is covered with the cylindrical hood 51.

There are further arranged an image processor (image processing computer) 70 for processing image data sent from the camera 50 through a cable 52, and a monitor 75 for displaying the image data and the result of inspection.

In this invention, the vertical axis of the bottle-cap assembly 30 is in agreement with the optical axis of the optical system (optical lens 40 and camera 50) and, besides, the illumination device is arranged to illuminate the cap mark and the bottle mark, whereby it is allowed to simultaneously shoot the bottle mark and the cap mark using the camera 50. Even when the bottle mark is positioned on the inside of the outer peripheral edge of the cap in the radial direction, the bottle mark can be shot together with the cap mark.

(Principle for Evaluating the Wrap-Fitted State of the Cap)

In the bottle-cap assembly 30 in which the cap is fitted to the bottle by being turned, the wrap-fitted state of the cap is evaluated based on the image data of the cap mark and the bottle mark imaged by the camera 50. That is, the positions of the cap mark and of the bottle mark are read onto a polar coordinate from the image shot by the camera 50, and, as required, are expanded to correctly evaluate the wrap-fitted state.

Figure 2:
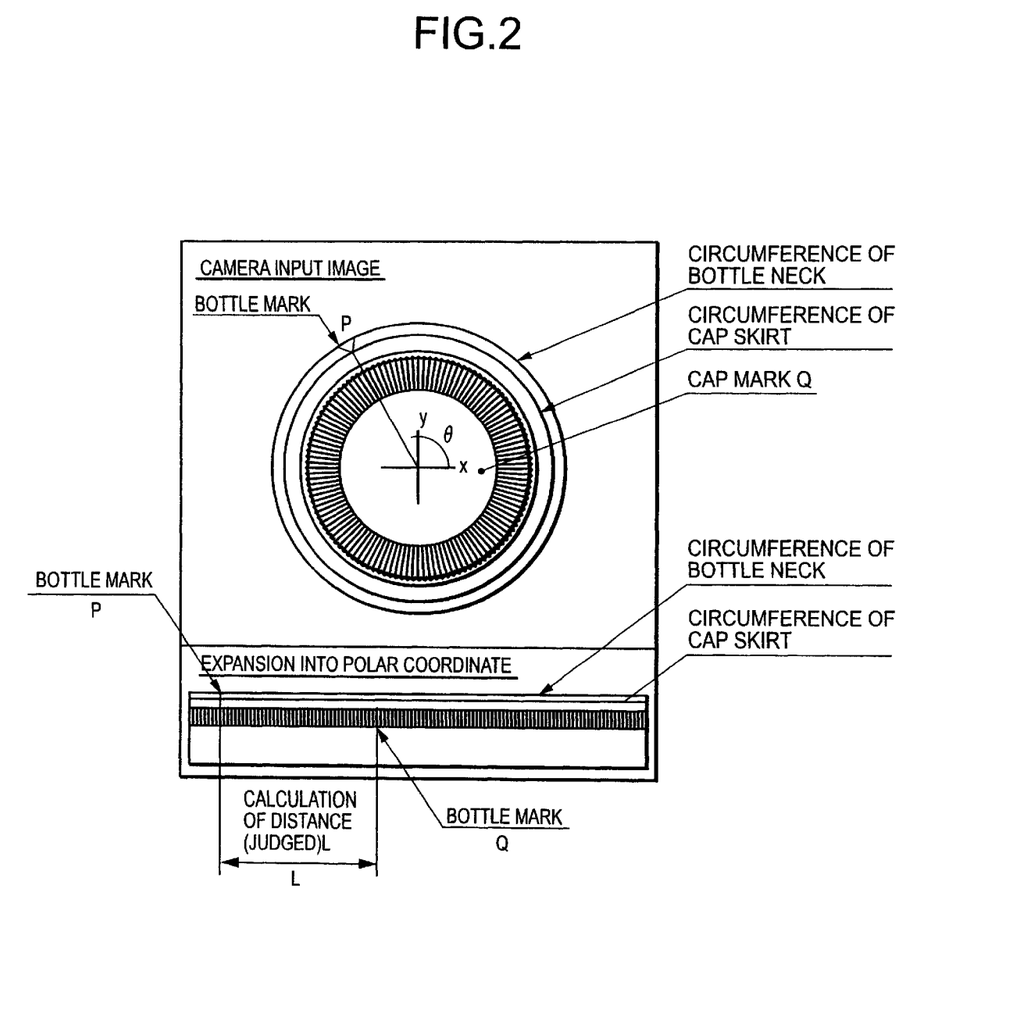
FIG. 2 is a view illustrating the principle of the inspection method of the present invention.

In FIG. 2 (cameral input image and expansion of polar coordinate) for illustrating the principle of evaluation, from a radius $r_1$ from the center and an angle $\theta_1$ from the x-axis, a position P of the bottle mark on the two-dimensional polar coordinate (on the camera input image) is expressed as, $$P(r_1, \theta_1)$$

where $x = r_1 \cos \theta_1$ and $y = r_1 \sin \theta_1$.

Further, from a radius $r_2$ from the center and an angle $\theta_2$ from the x-axis, a position Q of the cap mark on the two-dimensional polar coordinate (on the camera input image) is expressed as, $$Q(r_2, \theta_2)$$

where $x = r_2 \cos \theta_2$ and $y = r_2 \sin \theta_2$.

The wrap-fitted angle ($\theta$) of the cap mark based on the bottle mark is expressed by a formula (1), $$\theta = \theta_2 - \theta_1 \quad (1)$$

and the distance (L) on the expansion of the polar coordinate is expressed by a formula (2), $$L = r_1(\theta_2 - \theta_1) \quad (2)$$

Therefore, the wrap-fitted angle of the cap ($\theta^0$ which is also determined by the angle of the cap mark based on the bottle mark) of the bottle-cap assembly 30 in a suitably wrap-fitted state or the expanded distance ($L_0$) thereof is set in advance within a predetermined allowable range, and the wrap-fitted angle $\theta$ detected above is compared with the preset wrap-fitting angle $\theta_0$, or the expanded distance (L) that is detected is compared with the preset expanded distance ($L_0$) to detect whether the wrap-fitted state is acceptable.

In the description of the coordinate of FIG. 2, the direction of the angle is positive in the counterclockwise direction. In really fitting the cap, however, the cap is fitted by being turned in the clockwise direction. Therefore, the coordinate may be considered backside front.

As shown in FIG. 1, therefore, the optical axis of the optical lens 40 and of the camera 50 are brought into agreement with the vertical axis of the bottle-cap assembly 30, and the bottle mark P and the cap mark Q are simultaneously taken into the two-dimensional image through the camera 50. Thus, the relative positional relationship between the bottle mark P and the cap mark Q is detected through a simple image processing without effecting cumbersome and complex processing to detect whether the wrap-fitted state of the cap is acceptable.

(Bottle-Cap Assembly)

An example of the bottle-cap assembly 30 to which is applied the method of the invention will now be described with reference to FIGS. 3, 4 and 5, to which only, however, the invention is in no way limited though.

Figure 3:
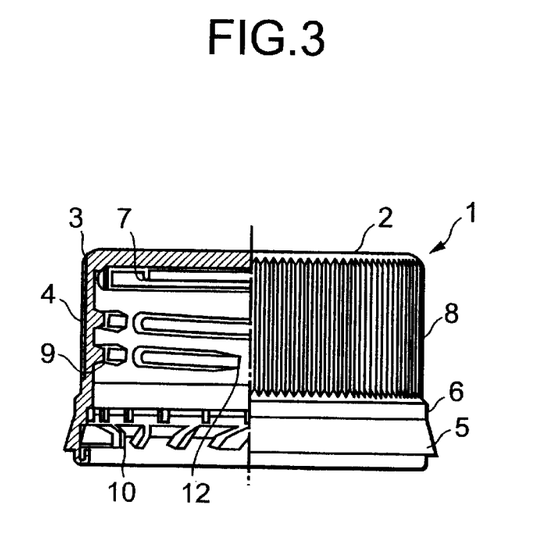
FIG. 3 is a view of a cap used in the present invention, the right half thereof being a side view and the left half thereof being a side sectional view.
Figure 4:
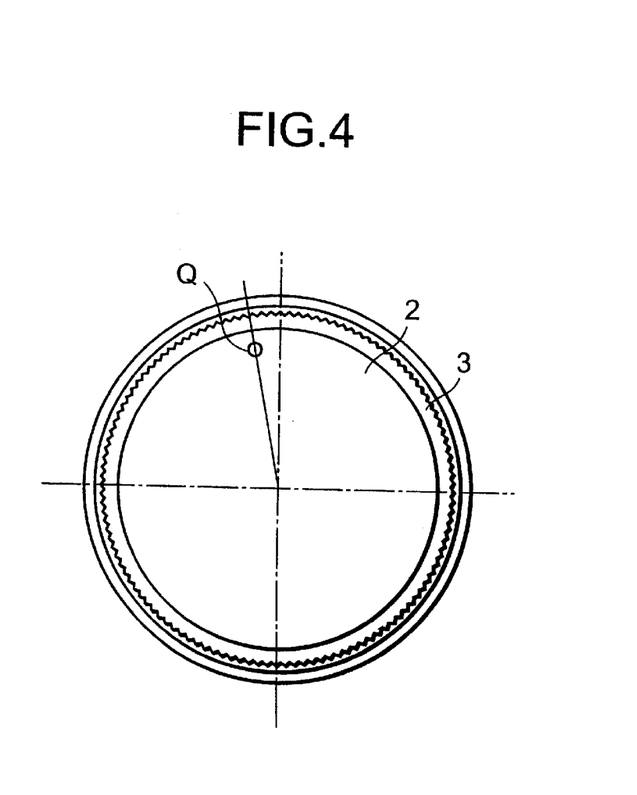
FIG. 4 is a top view of the cap of FIG. 3.

In FIGS. 3 and 4, the cap which is generally designated at 1 comprises a top panel 2 and a skirt 4 having hanging down from the top panel 2 via a corner portion 3 positioned along the peripheral edge of the top panel 2. A tamper-evidence (TE) band 5 is provided at the lower end of the skirt 4 via a weakened portion 6.

A liner member 7 is formed on the inner surface of the top panel 2 of the cap, and the outer peripheral protruded portion of the liner member comes in contact with the outer surface of the bottle neck to enhance the sealing of the container. The outer surface of the skirt 4 is knurled as designated at 8 for easy gripping, and the inner surface thereof is threaded as designated at 9 so as to be screwed onto the thread formed on the bottle neck.

Further, flap pieces 10 are formed on the inner surface of the TE band 5 so as to secure the TE band by being engaged with the beads of the bottle portion that will be described later.

Figure 5:
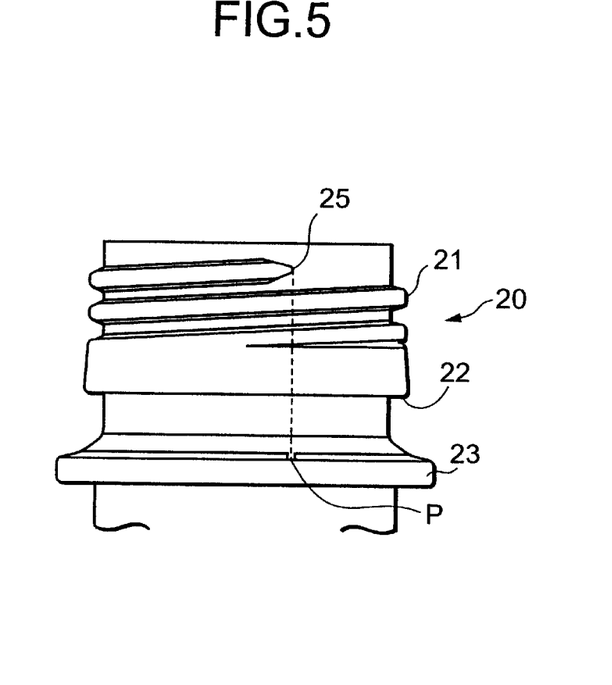
FIG. 5 is a partial side view illustrating the neck of a bottle to where the cap of FIG. 3 is fitted.

Referring to FIG. 5, the bottle used in the present invention has a bottle neck 20 which, though not shown, is integrally continuous to the shoulder portion, barrel and bottle portion like an ordinary bottle.

A threaded portion 21 is formed on the outer surface of the neck 20 so as to be screwed into the cap to seal the bottle. A stepped portion 22 is formed under the threaded portion 21 so as to be engaged with the flap pieces 10 of the TE band 5 of the cap. A support ring 23 is formed under the stepped portion 22 for holding the bottle at the time of filling and sealing.

The support ring 23 has an outer diameter equal to, or greater than, the outer diameter of the greatest portion under the cap 1 or under the TE band.

In the inspection method of the present invention, the cap mark Q and the bottle mark P are simultaneously imaged by using the camera 50 arranged over the bottle-cap assembly 30. For this purpose, the cap mark Q is formed on the peripheral edge of the top panel 2 of the cap, on the corner portion 3 between the top panel 2 and the skirt 4, or on the outer surface of the skirt 4. The bottle mark P is usually formed on the support ring 23 of the bottle. These marks are formed at predetermined portions as grooves or protuberances. Their shapes and sizes will be described later.

The cap is usually opaque enabling the mark to be easily recognized. As for the bottle, the whitened bottle neck 20 having the support ring 23 reflects light in large amounts enabling the mark to be easily detected compared to that of when the bottle neck is transparent. In the case of the bottle having the transparent bottle neck 20, light is reflected in small amounts, and it often becomes difficult to detect the mark. In such a case, therefore, there can be employed such means that coarsens the surface of the groove or of the protuberance forming the bottle mark P.

In FIG. 4, the cap mark Q is formed on the peripheral edge of the top panel 2, and the bottle mark P is formed on the upper surface or on the outer peripheral portion of the support ring 23 of the bottle.

These marks P and Q can be arranged at various positions so that the angle of wrap-fitting can be easily detected. In FIGS. 3 and 4, for example, the cap mark Q is formed at a position from where the threaded portion 9 starts on the inner surface of the skirt 4, i.e., formed on the peripheral edge of the top panel 2 of the cap corresponding to a position 12 from where the cap starts screwing onto the bottle.

On the other hand, the bottle mark P is formed at a position from where the threaded portion 21 starts on the bottle neck 20, i.e., formed on the outer periphery of the support ring 23 corresponding to a position 25 from where the bottle starts screwing into the cap.

Figure 6:
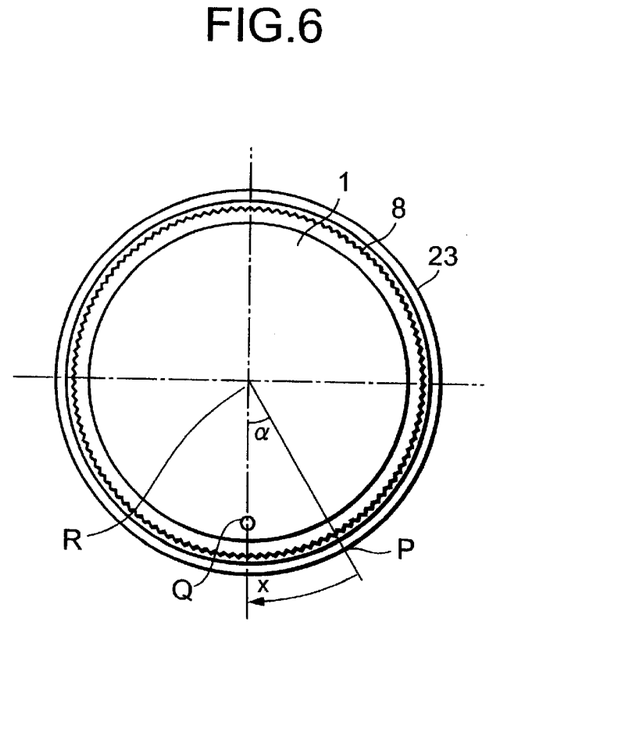
FIG. 6 is a view of when a bottle-cap assembly is viewed from the upper side.

In order to easily measure the angle of wrap-fitting indicated by the marks P and Q formed on the bottle and on the cap, further, though not necessarily required, there may be formed an auxiliary mark R at the center of the top panel 2 of the cap as shown in FIG. 6. Thus, the angle of wrap-fitting of the cap 1 in the bottle-cap assembly 30 can be easily measured relying upon the cap mark Q, auxiliary mark R and bottle mark P.

Namely, FIG. 6 is a plan view illustrating, on an enlarged scale, a portion of another bottle-cap assembly 30 which is the combination of a cap and a bottle. The cap 1 is wrap-fitted by being turned in the direction of an arrow X in the drawing. In this state, the bottle mark P formed on the support ring 23 of the bottle is at a lower-limit position capable of reliably guaranteeing the wrap-fitting of the cap. Even when the cap mark Q formed on the peripheral edge of the top panel of the cap exceeds the bottle mark P, there is no problem concerning the fitted state of the bottle-cap assembly 30 provided the cap mark Q lies within a predetermined range. In this state, as pointed out already, the auxiliary mark R is formed at the center of the top panel of the cap, and the wrap-fitted state can be confirmed relying upon an angle α defined by the bottle mark P, auxiliary mark R and cap mark Q.

In the present invention, the normal wrap-fitting position represented by the relationship of marks Q and P formed on the cap and on the bottle, is not limited to the above-mentioned embodiment only but various other embodiments can be employed.

Figure 7:
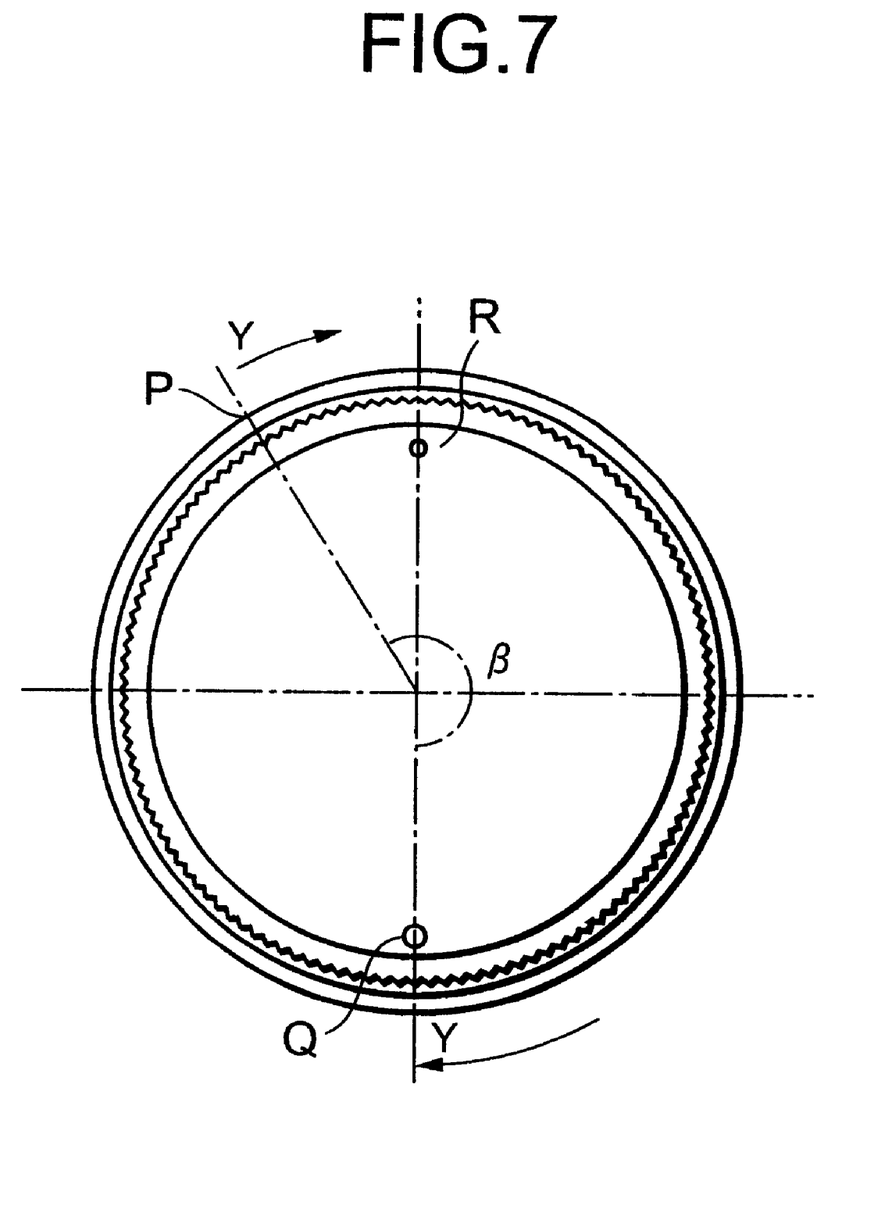
FIG. 7 is a view of when another bottle-cap assembly is viewed from the upper side.

Referring, for example, to FIG. 7, the bottle mark P may be formed at a position corresponding to the position from where the threaded portion starts (portion 25 shown in FIG. 5), and the cap mark Q may be formed at a position corresponding to a position from where the threaded portion starts (portion 12 in FIG. 2), so that it can be learned at a glance how much the cap is wrap-fitted depending upon the position of the cap mark Q with the bottle mark P as a reference. In FIG. 7, the angle β in a range of arrows Y—Y is the one for wrap-fitting. In the wrap-fitted state, it is determined in advance the angle β in what range is suited for the wrap-fitting. Then, the wrap-fitted state of the bottle-cap assembly is learned. In this case, the auxiliary mark R may be formed at a position symmetrical to the cap mark Q to facilitate the measurement of the angle β. The auxiliary mark R, too, can be formed as a recessed portion or as a protuberance like the marks P and Q.

In addition to those shown in FIGS. 6 and 7, the cap mark and the bottle mark may be so set as to come nearly at the same positions in a state where the bottle-cap assembly 30 is wrap-fitted.

The bottle-cap assembly 30 to which the inspection method of the invention is adapted, can be used for various bottles and caps.

The bottles may be draw-blown bottles made of a synthetic resin such as polyethylene terephthalate, and bottles produced by the injection-molding. The bottles may be glass bottles, as a matter of course.

The caps may be those of olefinic resins such as polyethylene, polypropylene, etc., those obtained by the compression-molding or injection-molding synthetic resins such as vinyl chloride resin or the like, as well as those of a metal such as aluminum or the like.

It is desired that the cap has the TE band integrally formed at the lower end of the cap through a weakened portion. The cap, however, may not have the TE band when it is covered with a shrink film after wrap-fitted.

(Lens)

Reverting to FIG. 1, it is desired that the lens 40 is a plano-convex lens or a meniscus convex lens having a diameter larger than that of the cap from the standpoint of vividly imaging not only the cap mark Q but also the bottle mark P.

Depending upon the size (diameter) of the support ring for forming the mark, the bottle mark P (a) may be positioned on the outer side of the outermost circumference of the cap in the radial direction, (b) may be overlapped on the outermost circumferential portion of the cap, or (c) may be positioned on the inner side of the outermost circumference of the cap in the radial direction. When the bottle mark P is in the cases (b) and (c), it is geometrically almost impossible to detect the bottle mark P from the upper side in the axial direction.

By using the plano-convex lens or the meniscus convex lens having a diameter larger than the diameter of the cap, however, it is allowed to form a clear image of the bottle mark P even in the above-mentioned cases (b) and (c) by guiding light traveling aslant toward the upper outer direction from the bottle mark P to enter into the lens, and by refracting light. Further, the area of light ray taken in from the bottle mark P can be widened, offering advantage from the standpoint of increasing the density of image of the bottle mark P and improving the contrast.

For example, the lens 40 is a plano-convex lens having a diameter larger than the diameter of the cap, i.e., having a diameter about three times as great as the diameter of the cap, and the plane surface of the plano-convex lens is facing the bottle-cap assembly 30. Desirably, the plano-convex lens has a diameter about 2 to about 4 times as large as the diameter of the cap. It is further allowable to enhance the focusing power from the bottle mark P by using the meniscus convex lens instead of using the plano-convex lens.

In the above inspection method, it is desired to so arrange the lens 40 that the cap mark Q and the bottle mark P are located within the photographing depth (also called the depth of a focus) of the lens 40.

When the focal distance is gradually extended to a distance, the lens becomes in focus up to infinity over a certain distance. This distance is called over-focal distance. If the focal distance of the lens is denoted by f, F-number (iris) of the lens by F, and allowable blurring by A, then, the over-focal distance ($f_h$) is expressed by the following formula (3), $$f_h = f^2/(A \times F) \tag{3}$$

As the allowable blurring (A), there is usually used a value 0.033.

The photographing depth stands for a range in which not only a subject is vividly imaged at a distance to which the focal point is adjusted but also ranges in front of, and at the back of, the above range in which the subjects are vividly imaged. A close limit (close point $d_1$) of the photographing depth and a distant limit (distant point $d_2$) of the photographing depth with respect to a distance ($d_0$) to which the focal point is adjusted and the over-foal distance ($f_h$), are given by the following formulas (4) and (5), $$d_1 = f_h \times d_0/(f_h + d_0) \quad (4)$$

$$d_2 = f_h \times d_0/(f_h - d_0) \quad (5)$$

According to the present invention as described above, the focal distance f of the lens is selected, the F-number (iris) of the lens is selected and the distance do to which the focal point is adjusted is selected, so that the cap mark Q and the bottle mark P enters into the photographing depth of the lens.
(Inspecting the Angle of Wrap-Fitting)

Figure 8:
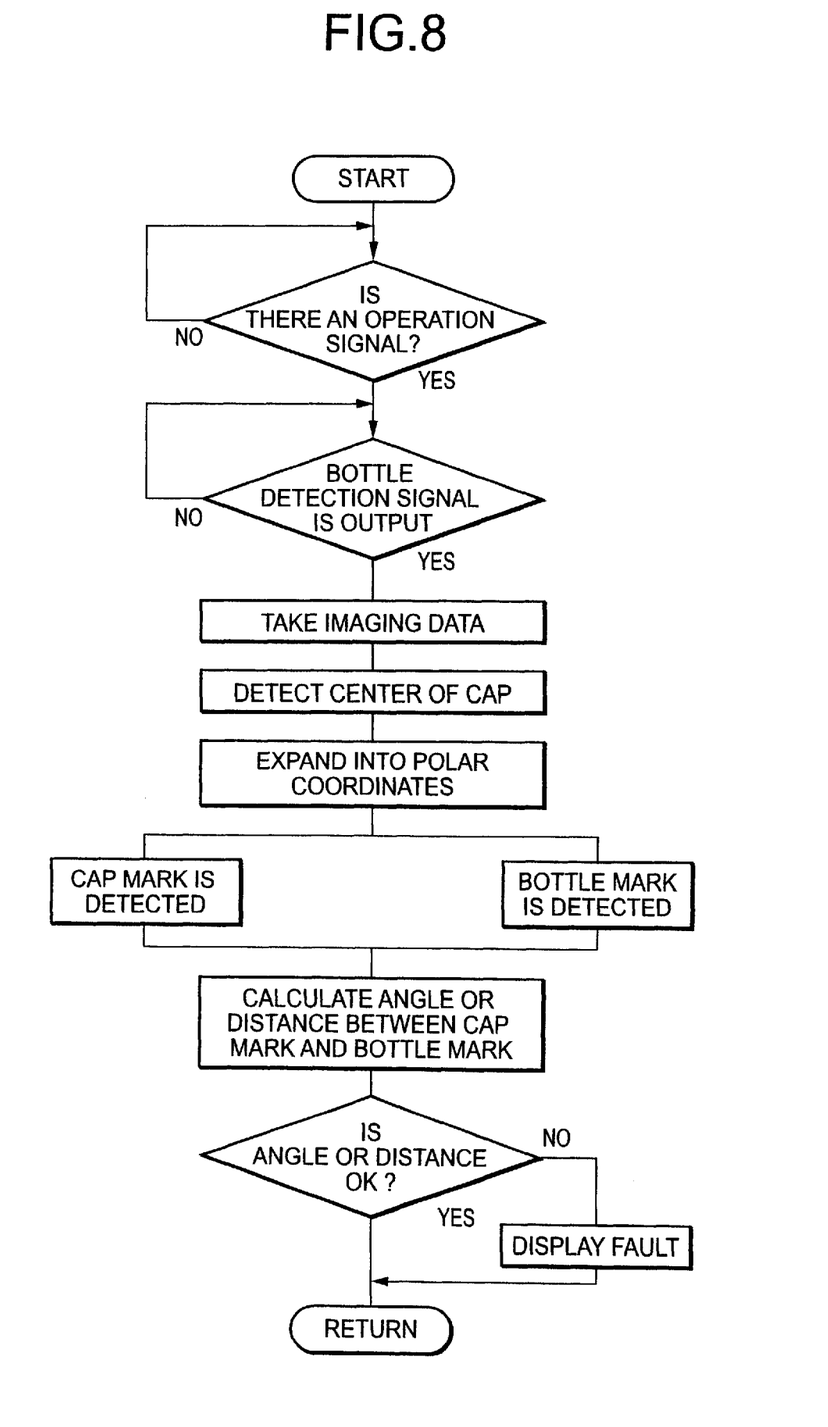
FIG. 8 is a flowchart illustrating the whole process of the inspection method of the present invention.

The angle of wrap-fitting the cap to the bottle-cap assembly 30 is inspected by the image processor (image processing computer) 70 and the camera 50 based on a flowchart shown in FIG. 8.

First, an operation signal of the inspection apparatus is detected. After the operation signal is detected, a signal of detecting the bottle-cap assembly 30 from the camera 50 is waited for. Upon receiving the detection signal, the image data from the camera 50 are sent to the image processor (image processing computer) 70. Based upon the image data, the center of the bottle-cap assembly 30 is detected. The center may be detected by forming the auxiliary mark R at the center of the top panel of the cap as described earlier or by effecting the centering from the circumference of the top plate of the cap.

After the center is detected, the image data on the two-dimensional coordinate are developed into polar coordinates as described in connection with FIG. 2 to thereby detect the cap mark Q and the bottle mark P.

From the position of the cap mark Q and the position of the bottle mark P detected on the polar coordinates, there is readily calculated the angle ($\theta$) or the distance (L) between the two, the detected angle $\theta$ of wrap-fitting is compared with the preset angle ($\theta_0$) of wrap-fitting, or the detected distance (L) is compared with the preset distance ($L_0$) to detect whether the wrap-fitting is acceptable. That is, when the angle or the distance lies outside the range, it means that the wrap-fitting state is faulty. When the angle or the distance lies within the range, the routine returns to the measurement of the next time.
(Illuminating Conditions)

When the inspection is conducted as described above, the bottle mark P and the cap mark Q must be vividly imaged by the camera 50. In the inspection apparatus of FIG. 1, therefore, the circular illuminating device 60 is arranged to surround the lens 40, and the camera 50 takes an image in an illuminated condition.

The illuminating device 60 may be the known one such as an LED, a fluorescent lamp or a halogen lamp. From the standpoint of adjusting the light path of the illuminating device 60, however, the LED is most desired as will be described below.

According to the present invention, it is desired that the illumination is obtained by using the illuminating device 60 so as to satisfy predetermined conditions.

Figure 9:
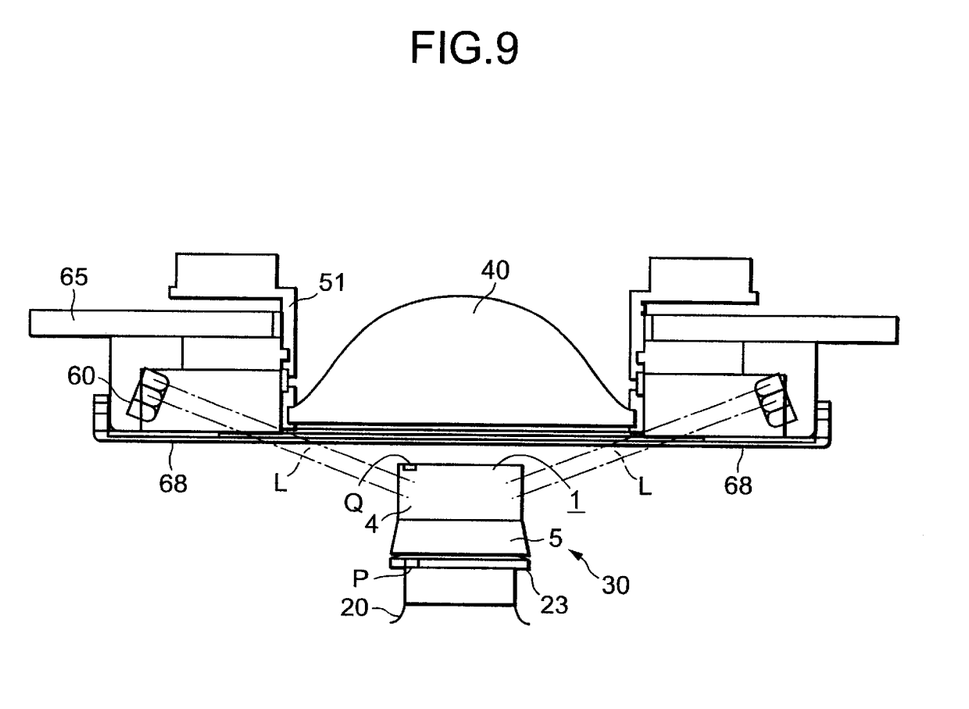
FIG. 9 is a view illustrating the illumination conditions favorably employed for the inspection method of the present invention.

That is, referring to FIG. 9 illustrating the illuminating conditions, the lens 40 is provided inside the opening at the lower end of the hood 51, and the illuminating device 60 is annularly provided on the outer side thereof via a suitable mounting plate 65 by using screws.

Under the lens 40, further, the bottle-cap assembly 30 is arranged as shown in FIG. 1.

In the present invention as shown in FIG. 9, a light-shielding plate 68 is mounted on the illuminating device 60, and light L from the illuminating device 60 is adjusted for its light path by the light-shielding plate 68 so as to be directly incident upon the skirt 4 of the cap 1. The cap mark Q has not been formed on the irradiated portion. Therefore, neither the cap mark Q nor the bottle mark P is directly irradiated with light.

In the present invention as described above, the image is taken by the camera 50 while permitting the skirt 4 of the cap 1 to be directly irradiated with light but without permitting the cap mark Q and the bottle mark P to be directly irradiated with light. Therefore, both the cap mark Q and the bottle mark P are caught as vivid images. If the cap mark Q and the bottle mark P are directly irradiated with light, these marks directly irradiated with light are caught as images having a very low contrast over the vicinity areas thereof, the discrimination thereof becomes difficult, and it becomes difficult to correctly conduct the above-mentioned image processing. Illumination that satisfies the above-mentioned conditions makes it possible to effectively avoid the above-mentioned inconvenience.

The cap mark Q may be formed on the outer surface of the skirt 4. In this case, as a matter of course, it becomes necessary to move the portion directly irradiated with light away from the portion where the cap mark Q is formed, so that the skirt 4 is directly irradiated with light.

In the present invention, the illumination is effected so as to satisfy the above-mentioned conditions to catch both the cap mark Q and the bottle mark P as vivid images. This advantage is not spoiled even when the invention is applied to a transparent bottle having a transparent neck 20 and a transparent support ring 23.

That is, in the case of a bottle having a transparent neck 20, the swinging level of the liquid contained in the bottle is reflected on the image of the bottle mark P, causing the image of the bottle mark P to be blurred and obscured. In this invention, on the other hand, the direct light from the illuminating device 60 falls on the skirt 4 of the cap 1 but is prevented from falling directly on the neck 20 of the bottle such as the support ring 23. Therefore, only a small quantity of light arrives at the liquid level in the bottle and, hence, light reflected by the liquid level is effectively suppressed. Accordingly, the swinging level of the liquid in the bottle is not reflected on the image of the bottle mark P. Even in the case of the transparent bottle, therefore, the bottle mark P is vividly imaged and is reliably discriminated.

Upon effecting the illumination so as to satisfy the above-mentioned conditions, the cap mark Q and the bottle mark P are vividly imaged at all times. Therefore, despite of using means for imaging the marks by using a single camera 50 from the upper side, there is obtained a distinguished advantage of reliably judging even a lack of the wrap-fitting by 360 degrees (one turn) of the cap.

Figure 10:
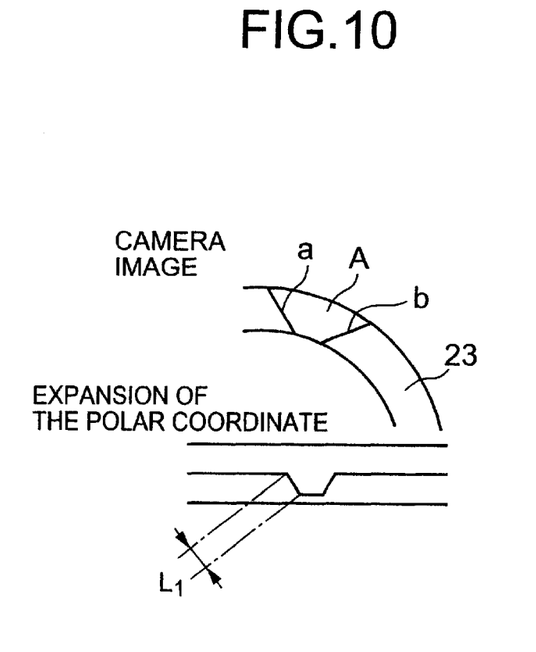
FIG. 10 is a view illustrating a major portion of the camera input image of the bottle-cap assembly to which the cap is properly wrap-fitted, and the expansion of a polar coordinate thereof.
Figure 11:
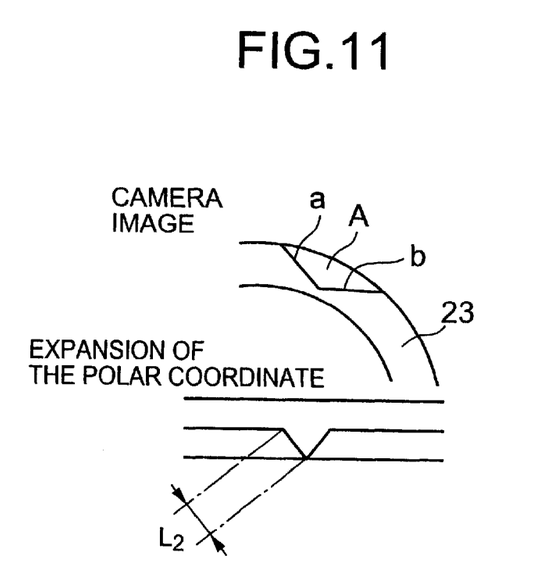
FIG. 11 is a view illustrating a major portion of the camera input image of the bottle-cap assembly of when the wrap-fitting of the cap is lacking one turn (360 degrees), and the expansion of a polar coordinate thereof.

FIGS. 10 and 11 are diagrams illustrating major portions of the images of the bottle-cap assemblies 30 input through the camera and the expansions of the polar coordinates thereof, wherein FIG. 10 is that of the bottle-cap assembly 30 to which the cap is normally wrap-fitted, and FIG. 11 is that of the bottle-cap assembly 30 to which the cap is insufficiently wrap-fitted by one turn (360 degrees). In FIGS. 10 and 11, symbol A denotes a recessed portion formed in the support ring 23 of the bottle, and either side a or b at both ends in the circumferential direction is recognized as the bottle mark P.

When the cap is normally wrap-fitted, the gap is very small between the support ring 23 of the bottle and the lower end of the cap (e.g., lower end of the TE band). As shown in FIG. 10, therefore, the central portion of the cap in the recessed portion A is not imaged but the portion of the support ring 23 on the side of the peripheral edge thereof only is vividly imaged. Therefore, the bottle mark P shown by the expansion of the polar coordinate has a short length $L_1$.

When the wrap-fitting of the cap is lacking by 360 degrees, on the other hand, the cap is floating off the bottle as compared to when it is normally wrap-fitted and, hence, a large gap is formed between the support ring 23 of the bottle and the lower end of the cap. Therefore, the recessed portion A as a whole is vividly imaged, and the mark P shown by the expansion of the polar coordinate has a large length $L_2$. Namely, there exists a relation $L_1 < L_2$.

According to the present invention, therefore, the length $L_1$ of the bottle mark P of when the cap is normally wrap-fitted is stored in the image processor and, hence, even a lack of wrap-fitting by 360 degrees is reliably judged from the relation to the length $L_1$.

(Cap Mark Q and Bottle Mark P)

In the inspection method of the present invention, the sizes and shapes of the cap mark Q and of the bottle mark P are so determined that clear and vivid images are obtained through the imaging by using the camera 50 and through the image processing.

For example, the cap mark Q is desirably formed as a circular recessed portion having a diameter of from about 0.5 to about 1.5 mm from the standpoint of recognizing the mark.

The bottle mark P is formed on the support ring 23 of the bottle as a recessed portion or a protuberance having a suitable width W (maximum length in the circumferential direction). Though there is no particular limitation on the shape as viewed from the upper side, the bottle mark P usually has a triangular shape or a rectangular shape such as a trapezoidal shape, an elongated shape or a parallelogram, and at least one of the pair of sides extending toward the inside of the bottle from the peripheral edges of the support ring 23 is recognized as the bottle mark P.

In wrap-fitting the cap to the bottle by turning the cap, it is necessary to hold the bottle by using a jig so that the bottle will not turn together with the cap. In this case, the nail mark of the jig is formed on the lower surface of the support ring 23. When the inspection method of the present invention is applied to the bottle of which the neck 20 has not yet been thermally crystallized but is still transparent, i.e., applied to the bottle having a transparent support ring 23, the nail mark of the jig is also caught as an image together with the bottle mark P, making it difficult to distinguish the bottle mark P from the nail mark of the jig.

Figure 12:
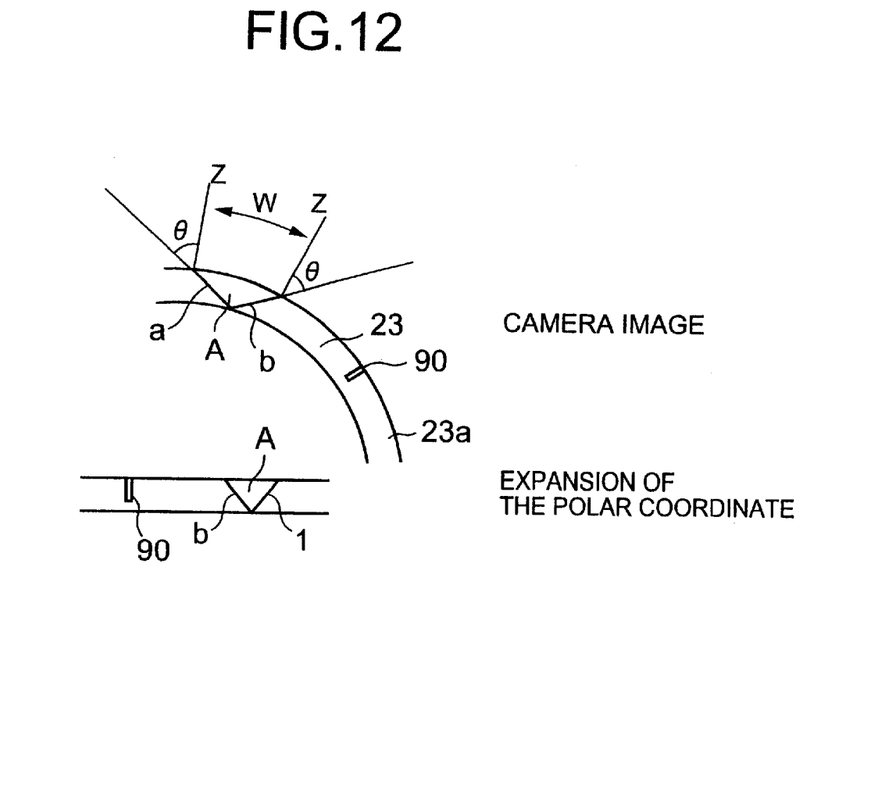
FIGS. 12 and 13 are views of camera images of a groove or a protuberance A used for recognizing the bottle mark P and the expansion of a polar coordinate, together with a nail mark of a jig formed in the lower surface of a transparent support ring.
Figure 13:
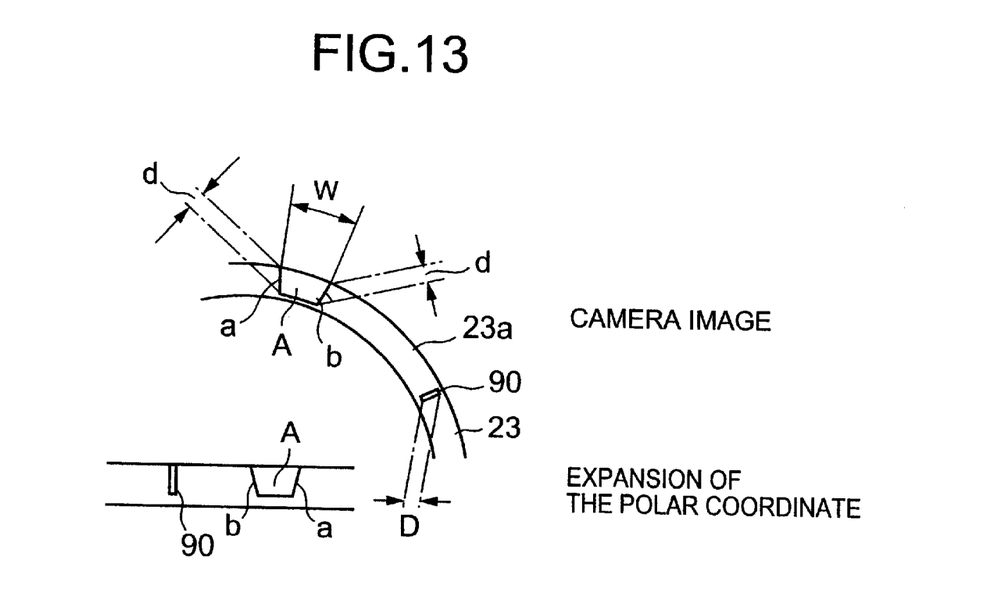

FIGS. 12 and 13 are diagrams illustrating the images through the camera of the recessed portion or of the protruded portion A utilized for recognizing the bottle mark P and the expansions of the polar coordinates thereof. In either of these drawings, the nail mark of the jig (designated at 90) is imaged. As for the shape of the recessed portion or the protuberance A formed on the upper surface of the support ring 23 as viewed from the upper side, a triangle with the peripheral edge 23a of the support ring 23 as a base is shown in FIG. 12, and a trapezoid with the peripheral edge 23a of the support ring 23 as a base is shown in FIG. 13.

In such a case, it is desired to recognize the bottle mark P by a method described below in order to clearly distinguish the bottle mark P from the nail mark of the jig.

Namely, in FIGS. 12 and 13, a maximum width w of the recessed portion or of the protuberance A in the circumferential direction is set to be from 3 to 8 mm, and is so programmed in the above-mentioned image processor 70 as to recognize the pair of sides a and b extending into the interior of the bottle from the peripheral edge of the support ring 23 as the bottle mark P.

The nail mark 90 of the jig formed on the lower surface of the support ring 23 is, in many cases, a substantially straight line as shown in FIGS. 12 and 13, and is extending toward the center of the bottle from the peripheral edge 23a of the support ring 23. Here, a combination of the pair of sides a and b of the recessed portion or of the protuberance A having a maximum width w in the circumferential direction, is recognized as the bottle mark P, making it possible to reliably distinguish the bottle mark P from the nail mark 90, to correctly detect relative positions of the bottle confirmation mark P and of the cap confirmation mark Q, and to correctly detect the wrap-fitted state of the cap.

In this method, when the maximum width w of the recessed portion or of the protuberance A in the circumferential direction becomes smaller than the above range, the gap between the pair of sides a and b to be recognized as the bottle mark P is so narrow that it becomes difficult to distinguish it from the nail mark 90. There is no meaning even if the maximum width w in the circumferential direction is increased to be greater than the above range, rather creating a large error in the position of the bottle mark P which is recognized as the pair of sides a and b and, further, and spoiling the appearance of the bottle. It is therefore desired that the maximum width w in the circumferential direction lies within the above-mentioned range.

Referring to FIG. 12, further, it is desired that the angle $\theta$ of inclination of the sides a and b (angle subtended by a straight line Z extending in the radial direction from the center of the bottle, i.e., subtended by a normal Z to the periphery of the support ring 23) is not smaller than 15 degrees, and is so programmed in the image processor 70 as to recognize the pair of sides a and b having the above-mentioned maximum width w and the angle $\theta$ of inclination as the bottle mark P.

That is, when the nail mark 90 is located close to either the side a or the side b (when, for example, the gap between the nail mark 90 and the side a or b is smaller than the above-mentioned maximum width w), it may happen that the pair of the nail mark 90 and the side a or b is incorrectly recognized as the bottle mark P. Here, however, the angle of inclination of the nail mark 90 with respect to the straight line Z is substantially zero. Upon setting the angle $\theta$ of inclination as a parameter for recognizing the bottle mark P, therefore, it is allowed to reliably avoid the above incorrect recognition. Usually, it is desired that the upper limit of the angle $\theta$ of inclination of the sides a and b is not larger than 75 degrees. If the angle $\theta$ of inclination is close to 90 degrees, it becomes difficult to distinguish the side a or b from the peripheral edge 23a of the support ring 23. Further, when the angle $\theta$ of inclination of the side a or b is used as a parameter for recognizing the bottle mark P, though there is no particular limitation, it is, usually, desired that the recessed portion or the protuberance A has a triangular shape as shown in FIG. 12.

In the present invention, further, it is also allowable to use the length d as a parameter for recognizing the bottle mark P instead of using the angle $\theta$ of inclination of the sides a and b. That is, as shown in FIG. 13, the lengths of the sides a and b are set to be not smaller than 2 mm, respectively, and are so programmed in the image processor 70 as to recognize the pair of sides a and b having the above-mentioned maximum width w and the length d as the bottle mark P.

That is, the nail mark 90 is caused by the jig that is used for preventing the bottle from turning, and its length D is relatively short and remains constant. Therefore, even by setting the length of the sides a and b to be larger than the length D of the nail mark 90, it is allowed to reliably avoid such inconvenience that the pair of the nail mark 90 and the side a or b is incorrectly recognized as the bottle mark P. The upper-limit value of the length d of the sides a and b is, usually, not larger than 4 mm. Even if the length d is set to be unnecessarily great, the recessed portion or the protuberance A formed on the support ring 23 simply becomes unnecessarily great. When the length d of the sides a and b is used as a parameter for recognizing the bottle mark P, though there is no particular limitation on the shape of the recessed portion or the protuberance A, it is generally desire that the recessed portion or the protuberance A has a rectangular shape such as a trapezoidal shape as shown in FIG. 13.

It is also allowable to have the bottle mark P recognized by using three parameters, i.e., by using the above-mentioned maximum width w, angle θ of inclination and length d. In this case, the recessed portion or the protuberance A may have a triangular shape or a rectangular shape as viewed from the upper side.

According to the present invention described above, it becomes possible to simultaneously shoot the bottle mark and the cap mark using a single camera and to correctly detect the positional relationship between the two.

Further, the cap mark and the bottle mark are imaged and are caught as vivid images under a condition where neither the cap mark nor the bottle mark is directly irradiated with light. Therefore, even when the support ring forming the bottle mark is transparent, it is allowed to correctly detect the positional relationship between the two marks and to precisely inspect the wrap-fitted state of the cap.

Moreover, a maximum width in the circumferential direction of the recessed portion or the protrusion formed on the upper surface of the transparent support ring is set to be not smaller than a predetermined value, and a combination of the pair of sides of when the recessed portion or the protrusion is viewed from the upper side is recognized as a bottle mark, making it possible to reliably distinguish the nail mark of the jig formed on the lower surface of the support ring from the bottle mark.

What is claimed is:

1. A method of inspecting a wrap-fitted state of a cap of a bottle-cap having a top panel and a skirt is wrap-fitted to a neck of a assembly in which the cap bottle, by detecting a positional relationship between a bottle mark formed on the bottle and a cap mark formed on the cap; wherein
    an optical lens is arranged at a higher position on a vertical center axis of said bottle-cap assembly in a manner that the vertical center axis is in agreement with an optical axis thereof;
    a single camera is arranged at a higher position on the optical axis of said optical lens to image the bottle mark and the cap mark through the optical lens;
    an illumination device is arranged for illuminating the bottle mark and the cap mark or the vicinities thereof; and
    the bottle mark and the cap mark are simultaneously shot by the camera, and the obtained image is sent to an image processor to detect a positional relationship between the bottle mark and the cap mark, wherein the bottle mark and the cap mark are read out from an image data received by the image processor into polar coordinates with the cap as a center and, as required, are expanded to detect the positions thereof, an angle between the bottle mark and the cap mark is calculated, and whether the wrap-fitted state is acceptable is judged relying upon the angle.

2. A method of inspection according to claim 1,
    wherein said bottle mark is a recessed portion or a protuberance having a maximum width (w) of from 3 to 8 mm in the circumferential direction of the support ring, and in imaging the recessed portion or the protuberance by using said camera, said bottle mark is so programmed in an image processor as to recognize, as the bottle mark, a combination of a pair of sides of the recessed portion or the protuberance extending inward from the peripheral edge of the support ring,
    wherein the illumination device is arranged to surround the optical lens, the optical path of light irradiated from said illumination device is so adjusted that the bottle mark and the cap mark are not directly irradiated with light but the portions of the skirt of the cap without forming the cap mark are directly irradiated with light, and the bottle mark and the cap mark are simultaneously shot by the camera while effecting the illumination by the illumination device under these conditions,
    wherein the neck of said bottle is transparent, and said bottle mark is formed in a peripheral edge portion on the upper surface of a transparent support ring formed on the neck.

3. A method of inspection according to claim 2, wherein a pair of sides of the recessed portion or of the protuberance has an angle (θ) of inclination of at least not smaller than 15 degrees with respect to a straight line extending in the radial direction from the center of the bottle, and are so programmed in the image processor as to recognize, as the bottle mark, said pair of sides based on said maximum width (w) and said angle (θ) of inclination.

4. A method of inspection according to claim 3, wherein said recessed portion or said protuberance has a triangular shape as viewed from the above.

5. A method of inspection according to claim 2, wherein a pair of sides of the recessed portion or of the protuberance has a length (d) of not smaller than 2 mm, and are so programmed in the image processor as to recognize, as the bottle mark, said pair of sides based on said maximum width (w) and said length (d).

6. A method of inspection according to claim 5, wherein said recessed portion or said protuberance has a rectangular shape as viewed from the above.

7. A device for inspecting a wrap-fitted state of a cap of a bottle-cap assembly in which the cap is wrap-fitted to a neck of a bottle, by detecting a positional relationship between a bottle mark formed on the neck of the bottle and a cap mark formed on the cap, comprising:
    an optical lens arranged at a higher position on a vertical center axis of said bottle-cap assembly in a manner that an optical axes thereof are in agreement;
    a single camera for simultaneously shooting the bottle mark and the cap mark through said optical lens;
    an illumination device for illuminating said bottle mark and said cap mark or the vicinities thereof; and
    an image processor for reading out the bottle mark and the cap mark from the image data shot by the camera, expanding, as required, the bottle mark and the cap mark to detect the positions thereof, calculating an angle between the bottle mark and the cap mark, and judging whether the wrap-fitted state is acceptable relying upon the angle.

8. A device for inspection according to claim 7, wherein the optical lens is a plano-convex lens or a meniscus convex lens having a diameter larger than the diameter of the cap.

9. A method of inspecting a wrap-fitted state of a cap of a bottle-cap having a top panel and a skirt is wrap-fitted to a neck of a assembly in which the cap bottle, by detecting a positional relationship between a bottle mark formed on the bottle and a cap mark formed on the cap; wherein an optical lens is arranged at a higher position on a vertical center axis of said bottle-cap assembly in a manner that the vertical center axis is in agreement with an optical axis thereof;

a single camera is arranged at a higher position on the optical axis of said optical lens to image the bottle mark and the cap mark through the optical lens;

an illumination device is arranged for illuminating the bottle mark and the cap mark or the vicinities thereof; and the bottle mark and the cap mark are simultaneously shot by the camera, and the obtained image is sent to an image processor to detect a positional relationship between the bottle mark and the cap mark, wherein the bottle mark and the cap mark are read out from an image data received by the image processor into polar coordinates with the cap as a center and, as required, are expanded to detect the positions thereof, a distance of expansion between the bottle mark and the cap mark is calculated, and whether the wrap-fitted state is acceptable is judged relying upon the expanded distance.

10. A method of inspection according to claim 9, wherein said bottle mark is a recessed portion or a protuberance having a maximum width (w) of from 3 to 8 mm in the circumferential direction of the support ring, and in imaging the recessed portion or the protuberance by using said camera, said bottle mark is so programmed in an image processor as to recognize, as the bottle mark, a combination of a pair of sides of the recessed portion or the protuberance extending inward from the peripheral edge of the support ring, wherein the illumination device is arranged to surround the optical lens, the optical path of light irradiated from said illumination device is so adjusted that the bottle mark and the cap mark are not directly irradiated with light but the portions of the skirt of the cap without forming the cap mark are directly irradiated with light, and the bottle mark and the cap mark are simultaneously shot by the camera while effecting the illumination by the illumination device under these conditions, wherein the neck of said bottle is transparent, and said bottle mark is formed in a peripheral edge portion on the upper surface of a transparent support ring formed on the neck.

11. A method of inspection according to claim 10, wherein a pair of sides of the recessed portion or of the protuberance has an angle ($\theta$) of inclination of at least not smaller than 15 degrees with respect to a straight line extending in the radial direction from the center of the bottle, and are so programmed in the image processor as to recognize, as the bottle mark, said pair of sides based on said maximum width (w) and said angle ($\theta$) of inclination.

12. A method of inspection according to claim 11, wherein said recessed portion or said protuberance has a triangular shape as viewed from the above.

13. A method of inspection according to claim 10, wherein a pair of sides of the recessed portion or of the protuberance has a length (d) of not smaller than 2 mm, and are so programmed in the image processor as to recognize, as the bottle mark, said pair of sides based on said maximum width (w) and said length (d).

14. A method of inspection according to claim 13, wherein said recessed portion or said protuberance has a rectangular shape as viewed from the above.

15. A device for inspecting a wrap-fitted state of a cap of a bottle-cap assembly in which the cap is wrap-fitted to a neck of a bottle, by detecting a positional relationship between a bottle mark formed on the neck of the bottle and a cap mark formed on the cap, comprising:

an optical lens arranged at a higher position on a vertical center axis of said bottle-cap assembly in a manner that an optical axes thereof are in agreement;

a single camera for simultaneously shooting the bottle mark and the cap mark through said optical lens;

an illumination device for illuminating said bottle mark and said cap mark or the vicinities thereof; and an image processor for reading out the bottle mark and the cap mark from the image data shot by the camera, expanding, as required, the bottle mark and the cap mark to detect the positions thereof, calculating a distance of expansion between the bottle mark and the cap mark, and judging whether the wrap-fitted state is acceptable relying upon the expanded distance.

16. A device for inspection according to claim 15, wherein the optical lens is a plano-convex lens or a meniscus convex lens having a diameter larger than the diameter of the cap.

* * * * *